(12) United States Patent
Fasano et al.

(10) Patent No.: US 11,926,849 B2
(45) Date of Patent: Mar. 12, 2024

(54) BIOSENSORS IN HUMAN GUT ORGANOIDS

(71) Applicants: The General Hospital Corporation, Boston, MA (US); MASSACHUSETTS INSTITUTE OF TECHNOLOGY, Cambridge, MA (US)

(72) Inventors: Alessio Fasano, Boston, MA (US); Timothy K. Lu, Cambridge, MA (US); Stefania Senger, Melrose, MA (US); Maria Eugenia Inda, Cambridge, MA (US)

(73) Assignees: The General Hospital Corporation, Boston, MA (US); Massachusetts Institute Of Technology, Cambridge, MA (US)

( * ) Notice: Subject to any disclaimer, the term of this patent is extended or adjusted under 35 U.S.C. 154(b) by 609 days.

(21) Appl. No.: 16/834,727

(22) Filed: Mar. 30, 2020

(65) Prior Publication Data
US 2020/0308549 A1 Oct. 1, 2020

Related U.S. Application Data

(60) Provisional application No. 62/826,352, filed on Mar. 29, 2019.

(51) Int. Cl.
*C12N 5/071* (2010.01)
*G01N 33/50* (2006.01)
*G01N 33/68* (2006.01)

(52) U.S. Cl.
CPC ....... *C12N 5/0679* (2013.01); *G01N 33/5044* (2013.01); *G01N 33/6803* (2013.01); *C12N 2501/998* (2013.01); *C12N 2503/02* (2013.01); *C12N 2506/03* (2013.01); *C12N 2513/00* (2013.01); *G01N 2500/10* (2013.01)

(58) Field of Classification Search
CPC ............ C12N 5/0679; C12N 2501/998; C12N 2503/02; C12N 2506/03; C12N 2513/00; C12N 2501/727; C12N 2533/90; G01N 33/5044; G01N 33/6803; G01N 2500/10; G01N 2800/065; G01N 2800/7095; G01N 33/5076; G01N 33/502
See application file for complete search history.

(56) References Cited

U.S. PATENT DOCUMENTS

| 8,163,537 B2 | 4/2012 | Martin et al. | |
|---|---|---|---|
| 2012/0196275 A1 | 8/2012 | Mezghanni et al. | |
| 2014/0038279 A1 | 2/2014 | Ingber et al. | |
| 2017/0191030 A1* | 7/2017 | Huch Ortega | C12N 5/0671 |
| 2017/0255857 A1 | 9/2017 | Collins et al. | |
| 2017/0335411 A1 | 11/2017 | Lu et al. | |
| 2017/0360850 A1 | 12/2017 | Lu et al. | |
| 2018/0002672 A1 | 1/2018 | Albritton et al. | |
| 2018/0072995 A1 | 3/2018 | Sato et al. | |

FOREIGN PATENT DOCUMENTS

WO  WO 2017/064421  4/2017

OTHER PUBLICATIONS

Rouch et al. "Development of Functional Microfold (M) Cells from Intestinal Stem Cells in Primary Human Enteroids."PLoS One. Jan. 28, 2016;11(1):e0148216. (Year: 2016).*
Jung et al. "In vitro and in vivo imaging and tracking of intestinal organoids from human induced pluripotent stem cells." FASEB J. Jan. 2018;32(1):111-122. (Year: 2018).*
Pletscher-Frankild et al. "DISEASES: text mining and data integration of disease-gene associations."Methods. Mar. 2015;74:83-9. (Year: 2015).*
Fasciano et al. "Induced Differentiation of M Cell-like Cells in Human Stem Cell-derived Ileal Enteroid Monolayers."J Vis Exp. Jul. 26, 2019;(149):10.3791/59894. (Year: 2019).*
Li et al. "Regulation of IL-8 and IL-1beta expression in Crohn's disease associated NOD2/CARD15 mutations."Hum Mol Genet. Aug. 15, 2004;13(16):1715-25. (Year: 2004).*
"Epithelial Histology." Acessed from http://courses.washington.edu/pbio375/epithelial-histology/epithelial-histology.html# on Oct. 27, 2022 (Year: 2022).*
PCT International Preliminary Report on Patentability in International Appln. No. PCT/US2020/025750, dated Oct. 14, 2021, 8 pages.
Abraham et al, "Mechanisms of disease," N. Engl. J. Med., Nov. 2009, 361:2066-2078.
Archer et al., "Engineered E. coli That Detect and Respond to Gut Inflammation through Nitric Oxide Sensing," ACS Synth Biol., 2012, 1(10):451-457.
Bartfeld et al., "In Vitro Expansion of Human Gastric Epithelial Stem Cells and Their Responses to Bacterial Infection," Gastroenterology, Jan. 2015, 148(1):126-136.e6.
Bush et al., "Transcriptional regulation by the dedicated nitric oxide sensor, NorR: a route towards NO detoxification," Biochem. Soc. Trans., Jan. 2011, 39(1):289-293.
Chanin et al., "Shigella flexneri Adherence Factor Expression in In Vivo-Like Conditions," mSphere, Nov. 2019, 4(6), 23 pages.
Corish et al., "Attenuation of green fluorescent protein half-life in mammalian cells ," Protein Engineering, Dec. 1999, 12(12):1035-1040.
Daeffler et al., "Engineering bacterial thiosulfate and tetrathionate sensors for detecting gut inflammation," Mol. Syst. Biol., 2017, 13(4):923, 14 pages.
Fiorentino et al., "Effect of wild-type Shigella species and attenuated Shigella vaccine candidates on small intestinal barrier function, antigen trafficking, and cytokine release," PLoS One, Jan. 2014, 9(1):e85211.
Forbester et al., "Derivation of Intestinal Organoids From Human Induced Pluripotent Stem Cells for Use as an Infection System," Methods Mol. Biol., Aug. 2016, 1576:157-169.
Freire et al., "Human gut derived-organoids provide model to study gluten response and effects of microbiota-derived molecules in celiac disease," Scientific Reports, 2019, 9(1):7029, 15 pages.

(Continued)

*Primary Examiner* — Titilayo Moloye
(74) *Attorney, Agent, or Firm* — Fish & Richardson P.C.

(57) ABSTRACT

Ex vivo monolayer models of human interstinal epithelia that express sensors, and methods of use thereof for evaluation of the effects of test compounds on the human gut.

7 Claims, 3 Drawing Sheets

(56) References Cited

OTHER PUBLICATIONS

Hensel et al., "The genetic basis of tetrathionate respiration in *Salmonella typhimurium*," Mol. Microbiol., Apr. 1999, 32(2):275-287.

Jung et al., "Isolation and in vitro expansion of human colonic stem cells," Nat. Med., Oct. 2011, 17(10):1225-1227.

Llanos-Chea et al., "Bacteriophage therapy testing against Shigella flexneri in a novel human intestinal organoid-derived infection model," Journal of pediatric gastroenterology and nutrition, Apr. 2019, 68(4):509-516.

Loftus et al., "Clinical epidemiology of inflammatory bowel disease: incidence, prevalence, and environmental influences," Gastroenterology, May 2004, 126(6):1504-1517.

Mimee et al., "An ingestible bacterial-electronic system to monitor gastrointestinal health," Science, May 2018, 360(6391):915-918.

Mimee et al., "Supplementary Materials for An ingestible bacterial-electronic system to monitor gastrointestinal health," Science, May 2018, 360(6391):915, 33 pages.

Molodecky et al, "Increasing Incidence and Prevalence of the Inflammatory Bowel Diseases With Time, Based on Systematic Review," Gastroenterology., Jan. 2012, 142(1):46-54.

Moon et al., "Development of a primary mouse intestinal epithelial cell monolayer culture system to evaluate factors that modulate IgA transcytosis," Mucosal Immunology, Jul. 2014, 7(4):818-828.

Muller et al., "Gene networks that compensate for crosstalk with crosstalk," Nature Communications, 2019, 10(1):4028, 8 pages.

Neuman et al., "Inflammatory bowel disease: role of diet, microbiota, life style," Transl. Res., Jul. 2012, 160(1):29-44.

Nigro et al., Intestinal Organoids as a Novel Tool to Study Microbes-Epithelium Interactions, Methods in Molecular Biology., 2019, 1576:183-194.

Ohno et al., "Intestinal M Cells," J. Biochem., Feb. 2016, 159(2):151-160.

PCT International Search Report and Written Opinion in International Appln. No. PCT/US2020/025750, dated Jul. 8, 2020, 10 pages.

Perli et al., "Continuous genetic recording with self-targeting CRISPR-Cas in human cells," Science, Sep. 2016, 353(6304).

Podolsky, et al., "Inflammatory bowel disease," N. Engl. J. Med., Sep. 1991, 325(13):928-937.

Price-Carter et al, "The alternative electron acceptor tetrathionate supports B12-dependent anaerobic growth of *Salmonella enterica* serovar typhimurium on ethanolamine or 1,2-propanediol," J. Bacteriol., Apr. 2001, 183(8):2463-2475.

Riglar et al., "Engineered bacteria can function in the mammalian gut long-term as live diagnostics of inflammation," Nat. Biotechnol., Jul. 2017, 35(7):653-658.

Rubens et al., "Synthetic mixed-signal computation in living cells," Nat. Commun., Jun. 2016, 7:11658, 10 pages.

Saffarini et al., "Involvement of Cyclic AMP (cAMP) and cAMP Receptor Protein in Anaerobic Respiration of Shewanella oneidensis," Bacteriol., 2003, 185(12):3668-3671.

Senger et al., "Human Fetal-Derived Enterospheres Provide Insights on Intestinal Development and a Novel Model to Study Necrotizing Enterocolitis (NEC)," Cell. Mol. Gastroenterol. Hepatol., Jan. 2018, 5(4):549-568.

Serena et al., "Intestinal Epithelium Modulates Macrophage Response to Gliadin in Celiac Disease," Nov. 2019, 6(167), 11 pages.

Tucker et al., "Analysis of the nitric oxide-sensing non-heme iron center in the NorR regulatory protein," J. Biol. Chem., Jan. 2008, 283(2):908-918.

VanDussen et al., "Development of an enhanced human gastrointestinal epithelial culture system to facilitate patient-based assays," Gut, Jun. 2015, 64(6):911-920.

Winter et al., "Host-Derived Nitrate Boosts Growth of *E. coli* in the Inflamed Gut," Science, Feb. 2013, 339(6120):708-711.

Wu et al., "Endogenous generation of hydrogen sulfide and its regulation in Shewanella oneidensis," Front Microbiol., Apr. 2015, 6:374.

Schwab et al., "Wnt is necessary for mesenchymal to epithelial transition in colorectal cancer cells," Developmental Dynamics, Mar. 2018, 247(3):521-530.

\* cited by examiner

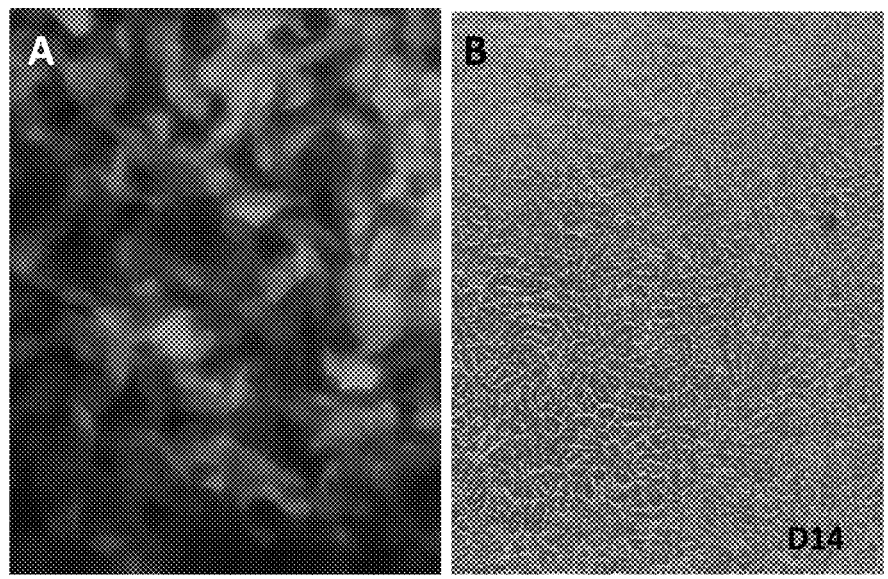
*FIGs. 4A-B*

BIOSENSORS IN HUMAN GUT ORGANOIDS

CLAIM OF PRIORITY

This application claims the benefit of U.S. Provisional Application Ser. No. 62/826,352, filed on Mar. 29, 2019. The entire contents of the foregoing are incorporated herein by reference.

FEDERALLY SPONSORED RESEARCH OR DEVELOPMENT

This invention was made with Government support under Grant No. DK048373 awarded by the National Institutes of Health. The Government has certain rights in the invention.

TECHNICAL FIELD

Described herein are ex vivo monolayer models of human interstinal epithelia that express sensors, and methods of use thereof for evaluation of the effects of test compounds on the human gut.

BACKGROUND

Inflammatory bowel disease (IBD) is a chronic, relapsing, intestinal disorder, frequently characterized as Crohn's disease or ulcerative colitis. These diseases are hallmarked by chronic inflammation, severe diarrhea with rectal bleeding, and malabsorption as a consequence of dysregulated intestinal immune homeostasis (Podolsky, et al., N. Engl. J. Med. 325, 928-937 (1991)). Disproportionate mucosal immune responses to resident bacteria due to genetic and environmental factors are thought to be crucially involved (Neuman et al, Transl. Res. 160, 29-44 (2012)). Chronic intestinal inflammation damages the epithelium and destroys the epithelial barrier, allowing more intestinal microbes to invade and evoking further immune responses (Abraham et al, N. Engl. J. Med. 361, 2066-2078 (2009)). Breaking this positive feedback loop is challenging with current approaches. IBD incidence in Western countries is increasing dramatically, with 2.2 million Europeans and 1.4 million Americans suffering from IBD (Loftus et al, Gastroenterology. 126, 1504-1517 (2004)). IBD is also increasing in newly industrialized countries in Asia, South America, and the Middle East (Molodecky et al, Gastroenterology. 142, 46-54 (2012)).

There is an unmet clinical need for new diagnostic and therapeutic approaches.

SUMMARY

Provided herein are ex vivo model systems, comprising a monolayer of differentiated mammalian, preferably human, epithelial cells, wherein the monolayer comprises enterocytes with microvilli, mucus-producing goblet cells, and Microfold (M) cells, having an apical surface and a basolateral surface, and wherein cells of the monolayer express one or more exogenous biosensors responsive to an inflammation-related signal comprising at least one promoter that binds to the inflammation-related signal and drives expression of a detectable output protein upon binding of the inflammation-related signal to the promoter.

In some embodiments, the monolayer is generated by a method comprising: obtaining primary stem cells from a mammalian subject; culturing the primary cells under conditions sufficient to allow proliferation of the cells and formation of organoids; seeding the cells into a culture plate comprising a permeable support device; maintaining the cells under conditions to allow for sufficient proliferation to form a monolayer having an apical and basolateral surface; contacting the apical surface with DAPT and the basolateral surface with RANKL, in amounts sufficient to induce differentiation of the cells to form enterocytes with microvilli, mucus-producing goblet cells, and M cells.

In some embodiments, the primary cells are obtained from the intestine of the subject. In some embodiments, the primary stem cells comprise intestinal crypt cells.

In some embodiments, the subject has an inflammatory gut condition, e.g., Irritable Bowel Disease (IBD), Irritable Bowel Sydnrome (IBS), or Celiac Disease (CD). In some embodiments, the IBD Crohn's disease or ulcerative colitis.

In some embodiments, the detectable output protein is a fluorescent protein.

In some embodiments, cells of the monolayer express a plurality of biosensors, wherein each biosensor drives a different detectable output. In some embodiments, the different detectable output proteins comprise a plurality of different fluorescent proteins of different colors.

In some embodiments, the biosensor is responsive to inflammation-related small molecule selected from nitric oxide, H2O2, thiosulfate, tetrathionate, AhR ligands, and heme, preferably wherein the small molecule is sensed using transcription factors that are responsive to the desired analytes (optionally NorV, oxySp*, katGp, PphsA342, PttrB185-269, PLux, and PL(HrtO)).

In some embodiments, the biosensor is responsive to nitric oxide and the promoter comprises transcriptional activator NorR.

In some embodiments, the biosensor is responsive to H2O2 and the promoter that drives expression of a detectable output protein comprises OxyR regulated oxyS promoter (oxySp) or katGp promoter, and the cell further consitutively expresses H2O2-sensitive transcription factor OxyR, wherein the presence of H2O2 oxidizes the OxyR and initiates transcription of the detectable output protein from the oxySp promoter or katGp promoter.

In some embodiments, the biosensor is responsive to an inflammation-related gene, preferably IL-1β, TNF-α, IFN-γ, IL-10, IL-12, IL-6, or IL-8, and the promoter comprises a promoter from the inflammation-related gene.

Also provided herein are methods for evaluating an effect of a test compound on mammalian intestinal inflammation. The methods can include providing an ex vivo model system as described herein; determining a baseline level of expression of detectable output protein from the biosensors in the ex vivo model system; contacting the ex vivo model system with the test compound; and detecting a second level of expression of detectable output protein from the biosensors in the presence of and/or after removal of, the test compound; wherein a change in the level of expression indicates that the test compound affects inflammation in the mammalian gut.

In some embodiments, increased levels of the detectable output proteins indicates an increase in inflammation, and: (i) the second level of expression is higher than the baseline level, then the test compound is identified as increasing inflammation in the mammalian gut; (ii) the second level of expression is below the baseline level, then the test compound is identified as decreasing inflammation in the mammalian gut; or (iii) the second level of expression is about the same as the baseline level, then the test compound is identified as not affecting inflammation in the mammalian gut.

In some embodiments, decreased levels of the detectable output proteins indicates an increase in inflammation, and: (i) the second level of expression is higher than the baseline level, then the test compound is identified as decreasing inflammation in the mammalian gut; (ii) the second level of expression is below the baseline level, then the test compound is identified as increasing inflammation in the mammalian gut; or (iii) the second level of expression is about the same as the baseline level, then the test compound is identified as not affecting inflammation in the mammalian gut.

In some embodiments, the ex vivo model system is generated by a method comprising obtaining primary cells from a subject who has an inflammatory gut condition, and a test compound that is identified as decreasing inflammation in the mammalian gut is a candidate therapeutic compound for the treatment of the inflammatory gut condition.

In some embodiments, a test compound that is identified as increasing inflammation in the mammalian gut is identified as an allergen or source of intolerance.

In some embodiments, the test compound is applied to the model system before, during, or after exposure to a known or suspected allergen, source of intolerance, or pro-inflammatory compound, and a change in levels of expression of detectable output proteins associated with inflammation indicates that the test compound ameliorates or exacerbates allergy, inflammation, or intolerance.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-B. A. Green Fluorescent Protein (GFP) expressed in organoid derived monolayers (D14) successfully transduced with a prototype of an engineered Lentivirus vectors carrying GFP gene under the promoter of the house keeping gene EF1a. B. Microphotography showing the cells depicted in A, in bright field, to visualize the cell monolayer.

DETAILED DESCRIPTION

Figure 1:
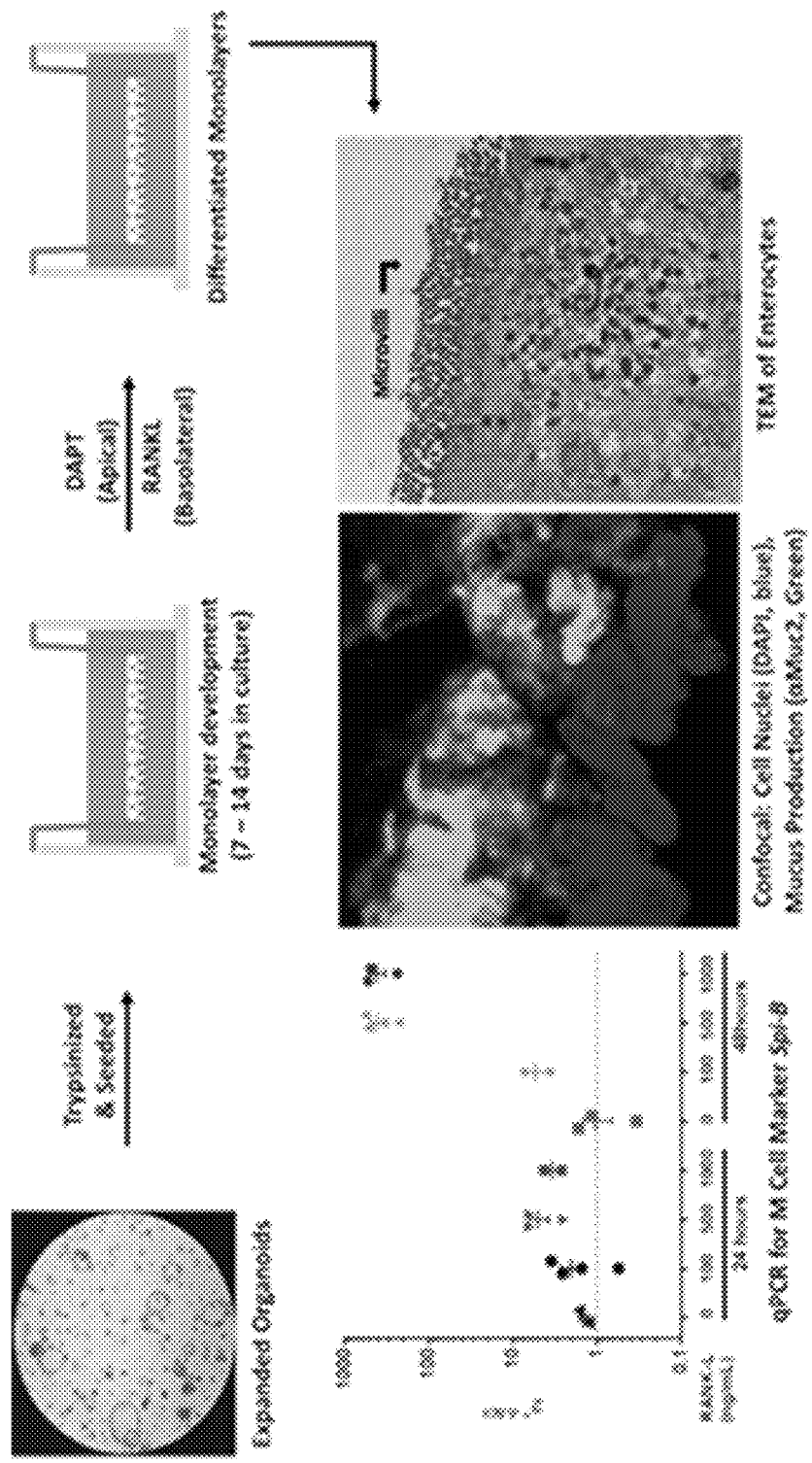
FIG. 1. Human Intestinal Organoid-Derived Epithelial Monolayer of the GI tract. Stem cells are isolated from patient biopsies, expanded, trypsinized, and seeded onto transwells. Following growth, DAPT (apical) and RANKL (basolateral) treatment induce differentiation to produce enterocytes with microvilli (TEM), mucus-producing goblet cells (confocal), and M cells (qPCR analysis for the M cell marker Spi-B following various concentrations of RANKL treatment for 24-48 hours. Plotted is the average relative fold increase over media control).

The present methods use human-derived gut organoid models from both healthy subjects and patients affected by inflammatory gut conditions (including IDB, celiac disease, and irritable bowel syndrome (MS)) to record inflammation signaling events into biosensors. These biosensors include promoters that sense the transcription of other genes induced by intestinal microbiota in primary gut epithelial cells, using various detectable outputs, providing real-time readouts of cellular responses in a physiologically relevant model.

These sensor technologies facilitate characterization of inflammatory processes, e.g., during the onset of chronic inflammation. In addition, the specialized genetic circuits can query specific biological events and record this information into DNA-based memory. The biosensor circuits can sense microbiome-host interaction events, and 2) caspase activities that reflect inflammasome activation. Other signals relevant to IBD can be incorporated into the sense and record and response platform.

GI Models

The present methods make use of human intestinal organoid-derived epithelial monolayers as model systems of the GI tract. Primary intestinal cell lines derived from the duodenum, terminal ileum, cecum, and ascending colon of healthy donor or affected subject biopsies or tissue can be used as the starting material. The material can be obtained from adults or children (e.g., under the age of 13 years). Propagating these primary lines in 3-D culture (organoids) generates fully differentiated, polarized, and functional cells (see, e.g., US20180072995); however, the cells cannot be easily exposed to pathogens on the apical surface. To overcome this limitation, monolayers can be generated from the organoids in a transwell system; and provide an effective in vitro model to study infectious disease and interrogate the pathophysiology of human disease. This human intestinal organoid-derived epithelial monolayer (HIODEM) model can be used to capture vital data, such as transepithelial electrical resistance (TEER) and secreted cytokine profiles (Fiorentino et al, PLoS One. 9(1):e85211 (2014)) from non-cancerous cells in a human in vivo-like environment.

These models can be generated as follows. Intestinal crypt stem cells are isolated from patient biopsies (e.g., from normal healthy subjects and those with including IBD, celiac disease (CD), and irritable bowel syndrome (IBS)). The cells are expanded in matrigel to generate organoids, that are subsequently trypsinized, and seeded onto transwells (or other culture plates comprising a permeable support device, e.g., as described in U.S. Pat. No. 8,163, 537). After sufficient growth, deprivation of stem cell factors, and addition of a gamma secretase inhibitor (e.g., DAPT) (apical, to promote differentiation of goblet cells) and RANKL (basolateral) treatment induce differentiation to produce enterocytes with microvilli (detectable using TEM), mucus-producing goblet cells (detectable using confocal), and M cells. For modeling the terminal ileum and colon of the GI tract, human enterocytes, mucus-producing goblet cells, and antigen sampling M cells are present in the cultures. See, e.g., VanDussen et al., Gut. 2015 June; 4(6):911-20 (2015); Senger et al., Cell Mol Gastroenterol Hepatol. 5(4):549-568 (2018); Freire et al., Scientific Reports 9(1):7029 (2019); US20120196275; and US20140038279.

This system overcomes the drawbacks of spheroid systems (Nigro et al., Methods in molecular biology. Methods Mol Biol. 2019; 1576:183-194 (2016); Bartfeld et al., Gastroenterology. 148(1):126-36 e6 (2015); Forbester et al., Methods Mol Biol. 1576:157-169 (2019)), which require microinjection of pathogens and are not suited to high-throughput analyses. The epithelial cells in the monolayer polarize and differentiate, as determined by TJ protein (ZO-1) immunostaining and TEER. The monolayer contains other differentiated cells, as seen by positivity for the markers sucrase-isomaltase (mature enterocytes), chromogranin A (enteroendocrine cells), UEA-1 (M-cells), and MUC-2 (differentiated goblet cells) (Senger et al., Cellular and Molecular Gastroenterology and Hepatology. 2018; 5(4):549-68). When challenged with bacteria, the model aptly responds to infection (Chanin et al., mSphere. 2019 Nov. 13; 4(6); Llanos-Chea et al., Journal of pediatric gastroenterology and nutrition. 2019; 68(4):509-16); and innate immune responses are activated as measured by increased IL-8 expression (Senger et al., 2018). These observations validate HIODEM as a suitable model system of human disease.

Biosensors

The present methods make use of biosensors that include promoters that sense the presence of biomarkers of inflammation in primary gut epithelial cells (e.g., small molecules or proteins), using various detectable outputs, e.g., fluorescent proteins, driven by relevant promoters. Endogenous or synthetic promoters can be used to drive the expression of the detectable output. Small molecules including nitric oxide, H2O2, thiosulfate, tetrathionate, AhR ligands, and heme, can be sensed using transcription factors/promoters that are responsive to the desired analytes (e.g., NorR, OxyR, ThsRS, TtrRS, LuxR, HrtR). Circuit performance can be optimized by modulating regulatory parts (e.g., promoters, plasmid copy number, RBS, recombinases) and circuit topology (e.g., open loop, positive feedback, negative feedback).

Natural systems that sense biomarkers of inflammation, such as nitric oxide (Archer et al, ACS Synth Biol. 1(10): 451-457 (2012)), thiosulfate and tetrathionate (Daeffler et al, Mol Syst Biol. 13(4): 923 (2017)), can be adapted for use as biosensors in the present methods and compositions. In the described tetrathionate and nitric oxide bacterial biosensors, sensing events were recorded by genetic memory circuits causing the permanent activation of gene expression via bistable toggle switches; in the present methods, a CRE system can be used to make permanent modifications to the genome. These biosensors can be adapted to drive expression of a detectable output gene instead of the memory circuit.

In the present methods, these biosensors can include inflammation-induced systems that can be adapted to be expressed in mammalian cells, see, e.g., US 2017/0360850 (describing genetically engineered sensors for detection of hydrogen peroxide, nitric oxide, inflammatory cytokines such as IL-6, IL-18, or TNF-alpha), US 2017/0335411 (describing genetically engineered sensors for detection of signals including chemical signals), and US 2017/0255857 (describing genetically engineered analog-to-digital biological converter switches and their use in biological systems including as sensors), and Perli et al., Science. 2016 Sep. 9; 353(6304) (leveraging self-targeting guide RNA (stgRNA)/Cas9 to detect TNFα concentrations. This system can be modified to replace the Cas9 with a reporter gene). In some embodiments, the sensor includes a simple circuit, wherein a single transcription factor detects (binds) a signal associated with inflammation (e.g., a signal that drives expression of an inflammation-related gene, e.g., IL-1β, TNF-α, IFN-γ, IL-10, IL-12, IL-6, and IL-8), activates its promoter and drives expression of a detectable output upon binding of the signal.

Alternatively, a sensor circuit can be more complex, comprising: a first promoter operably linked to a nucleic acid encoding a regulatory protein responsive to an input signal associated with inflammation, and a second promoter responsive to the regulatory protein and operably linked to a nucleic acid encoding an output protein, e.g., a detectable output, wherein activity of the second promoter is altered (e.g., increased or decreased) when bound by the regulatory protein.

In some embodiments, the output protein is not detectable, but is flanked by a set of regulatory sequences, wherein the regulatory sequences interact with the first output protein to operably link the output molecule to a third promoter, which can in turn drive an output protein, e.g., a detectable output, or an output that activates a third circuit, and so on, e.g., as described in US 20170360850.

To ensure the reporters reflect dynamic changes in gene transcription, the sensors can include fast-degradation tags (e.g., CDB or PEST domains (Corish et al., Protein engineering 12(12):1035-40 (1999)) on the output proteins, e.g., fluorescent proteins. See, e.g., FIG. 2.

The biosensors can be constitutively expressed in the cells of the model, e.g., from a stably integrated or episomal biosensor transgene. The biosensor transgene can be delivered to the cells using methods known in the art, e.g., viral or plasmid delivery. Viral delivery vectors useful in the present methods include recombinant retrovirus, adenovirus, adeno-associated virus, alphavirus, and lentivirus.

A plurality of biosensors, e.g., each driving a different detectable output (e.g., a different colored fluorescent protein) can be expressed in the cells of the model.

IL-8

Figure 2:
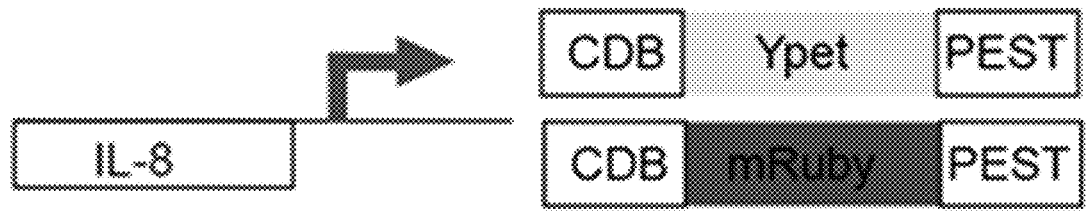
FIG. 2. Transcription-coupled expression of different fluorescent proteins with degradation tags on N (CDB) and C (PEST) termini.

IL-8 is a transcriptional target activated by NF-κB inflammation signaling. A biosensor to detect transcription of IL-8 can include a reporter protein driven by a human IL-8 promoter, e.g., as shown in FIG. 2. Other cytokines can be detected similarly.

Nitric Oxide Sensing.

Inflamed epithelial cells produce nitric oxide by up-regulating inducible nitric oxide synthase (iNOS), an enzyme that produces nitric oxide from L-arginine. Though nitric oxide is used as an inflammatory signal in mammals, many bacteria possess nitric oxide sensors, often to control the expression of cognate nitric oxide reductases that metabolize and detoxify nitric oxide. The bacterial transcriptional activator NorR is preferred, as it reacts solely with nitric oxide and no other reactive nitrogen species (NOx) (Bush et al. Biochem. Soc. Trans. 39, 289-293 (2011), Tucker et al. J. Biol. Chem. 283, 908-918 (2008)).

A system for recording nitric oxide production based on a previously characterized nitric oxide sensor (Archer, ACS Synth Biol. 1(10): 451-457 (2012)) can be used. An exemplary sensor combines nitric oxide sensing through NorR with a DNA recombinase core circuit by placing transcription of a reporter gene under the control of NorR regulated norV promoter (PnorV) on the same low-copy plasmid.

Rather than using the sequence for the native ribosomal binding site (RBS) for norV, a stronger synthetic RBS (BBa_B0064 from the BioBrick Parts Registry) can be used.

Peroxide Sensing

Figure 3A:
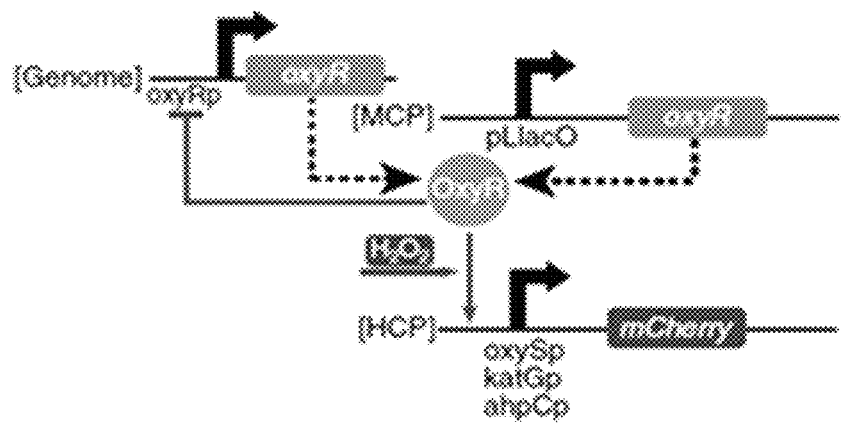
FIGS. 3A-B. H2O2-sensing synthetic gene circuits. A. The open-loop circuit used to test different H2O2-OxyR regulated promoters. OxyR is expressed from an unregulated constitutive pLlacO promoter on a medium-copy plasmid (MCP), and mCherry is expressed from different OxyR-activated promoters on a high-copy plasmid (HCP). OxyR activates mCherry expression in the presence of H2O2. B. Empirical H2O2-mCherry transfer functions for three different promoters (oxySp in blue, katGp in orange, ahpCp in purple).
Figure 3B:
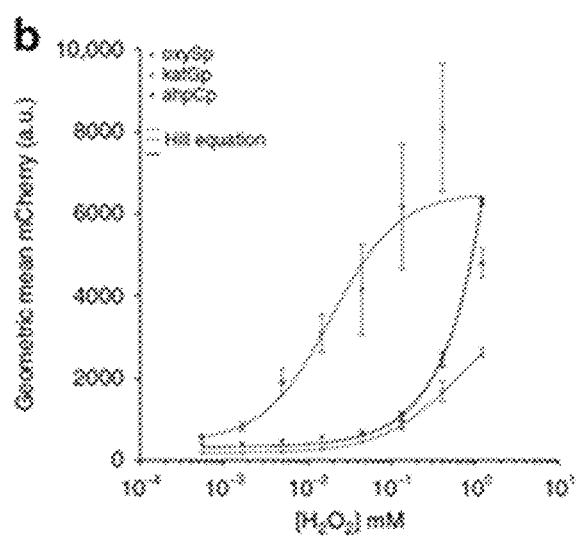

H2O2 plays intricate biological roles across all kingdoms of life, and its regulation is linked to human health and disease. H2O2 oxidizes and activates the *Escherichia coli* transcription factor OxyR. OxyR can be constitutively expressed to set a minimum concentration of OxyR in the cell, since genomically expressed oxyR is auto-negatively regulated, and a reporter sequence can be placed under the control of the OxyR regulated oxyS promoter (oxySp) or katGp promoter, e.g., on the same low-copy plasmid (Rubens et al, Nat Commun. 2016 Jun. 3; 7:11658 (2015); Muller et al. Nature communications. 10(1):4028 (2019)). See, e.g., FIGS. 3A-B.

Thiosulfate and Tetrathionate Sensing

ThsRS is the only genetically encoded thiosulfate sensor (characterized in Daeffler 2017). The other known genetically encoded tetrathionate sensor is the TtrSR two-component system (TCS) from *S. typhimurium* (Hensel et al, Mol Microbiol. 32(2):275-87 (1999); Price-Carter et al, J Bacteriol. 183(8):2463-75 (2001); Riglar et al., Nat Biotechnol. 35(7):653-658 (2017)). This TCS comprises TtrS, a membrane-bound sensor histidine kinase (SK) that phosphorylates the cytoplasmic response regulator (RR) TtrR in the presence of tetrathionate. Phosphorylated TtrR (TtrR-P) activates transcription of the tetrathionate reductase operon, ttrBCA, via the ttrB promoter (PttrB). However, PttrB is repressed by $O_2$ and nitrate via the global regulator FNR and an unknown pathway, respectively (Price-Carter et al, 2001). Furthermore, FNR is required for transcription from PttrB (Price-Carter et al, 2001), eliminating the possibility of avoiding $O_2$ cross-repression by deleting this repressor. Though gut $O_2$ levels are incompletely understood and an area of active study, they may be relatively high near the epithelial mucosal boundary due to proximity to the blood. Furthermore, gut nitrate levels have been shown to be elevated during inflammation (Winter et al, Science. 339 (6120):708-11 (2013)). Thus, the unwanted cross-regulation of *S. typhimurium* TtrSR could comprise its performance as a gut tetrathionate sensor.

The *S. baltica* TtrSR and *S. halifaxensis* TtrRS sensors are free from nitrate cross-repression and function in the presence and absence of oxygen. These benefits stem from the differences in the Shewanella respiration regulatory network relative to other facultative anaerobes, whereby gene expression of anaerobic reductases is coordinated by CRP rather than the oxygen regulator FNR or the redox regulator ArcBA (Saffarini et al, Bacteriol, 185 (12), 3668-71 (2003); Wu et al, Front Microbiol. 6:374 (2015)).

Quantification of Cytokines

Production of pro-inflammatory cytokines IL-1β, TNF-α, IFN-γ, IL-10, IL-12, IL-6, and IL-8 in the gut organoid-derived cultures can also be analysed, e.g., using biosensors or other known methods.

Detectable Outputs—Reporter Proteins

A number of reporter proteins are known in the art, and include green fluorescent protein (GFP), variant of green fluorescent protein (GFP10), enhanced GFP (eGFP), TurboGFP, GFPS65T, TagGFP2, mUKGEmerald GFP, Superfolder GFP, GFPuv, destabilised EGFP (dEGFP), Azami Green, mWasabi, Clover, mClover3, mNeonGreen, NowGFP, Sapphire, T-Sapphire, mAmetrine, photoactivatable GFP (PA-GFP), Kaede, Kikume, mKikGR, tdEos, Dendra2, mEosFP2, Dronpa, blue fluorescent protein (BFP), eBFP2, azurite BFP, mTagBFP, mKalamal, mTagBFP2, shBFP, cyan fluorescent protein (CFP), eCFP, Cerulian CFP, SCFP3A, destabilised ECFP (dECFP), CyPet, mTurquoise, mTurquoise2, mTFPI, photoswitchable CFP2 (PS-CFP2), TagCFP, mTFP1, mMidoriishi-Cyan, aquamarine, mKeima, mBeRFP, LSS-mKate2, LSS-mKatel, LSS-mOrange, CyOFP1, Sandercyanin, red fluorescent protein (RFP), eRFP, mRaspberry, mRuby, mApple, mCardinal, mStable, mMaroonl, mGarnet2, tdTomato, mTangerine, mStrawberry, TagRFP, TagRFP657, TagRFP675, mKate2, HcRed, t-HcRed, HcRed-Tandem, mPlum, mNeptune, NirFP, Kindling, far red fluorescent protein, yellow fluorescent protein (YFP), eYFP, destabilised EYFP (dEYFP), TagYFP, Topaz, Venus, SYFP2, mCherry, PA-mCherry, Citrine, mCitrine, Ypet, IANRFP-AS83, mPapayal, mCyRFP1, mHoneydew, mBanana, mOrange, Kusabira Orange, Kusabira Orange 2, mKusabira Orange, mOrange 2, mKOK, mKO2, mGrapel, mGrape2, zsYellow, eqFP611, Sirius, Sandercyanin, shBFP-N158S/L173I, near infrared proteins, iFP1.4, iRFP713, iRFP670, iRFP682, iRFP702, iRFP720, iFP2.0, mIFP, TDsmURFP, miRFP670, Brilliant Violet (BV) 421, BV 605, BV 510, BV 711, BV786, PerCP, PerCP/Cy5.5, DsRed, DsRed2, mRFP1, pocilloporin, Renilla GFP, Monster GFP, paGFP, or a Phycobiliprotein, or a biologically active variant or fragment of any one thereof. Other proteins such as luciferase can also be used.

Methods of Use

The present models can be used to screen potential therapeutic compounds, e.g., in pre-clinical studies aimed at developing new therapeutic strategies, for a variety of chronic inflammatory gut diseases, including IBD, IBS, and celiac disease (CD). Currently we rely on animal models that not always recapitulate the human disease and, therefore, promising drugs resulting effective in animal models fail when tested in humans. The present methods can minimize this risk by offering a model that is not only closely pertinent to human diseases but also capable of identifying specific therapeutic targets to ameliorate the inflammatory process in a variety of chronic inflammatory diseases.

Included herein are methods for screening various test compounds, e.g., polypeptides, polynucleotides, inorganic or organic large or small molecules, or various probiotics or microbes (e.g., identified populations of microbes), to identify agents useful in the treatment of disorders associated with inflammatory gut conditions, e.g., IBD, IBS, or CD. In some embodiments, the test compound is a known or potential allergen, e.g., is or is derived from celery; cereals containing gluten, e.g., wheat (e.g., spelt and Khorasan), rye, barley and oats; crustaceans (e.g., prawns, crabs and lobsters); eggs; fish; lupin; milk; molluscs—such as mussels and oysters; mustard; tree nuts—including almonds, hazelnuts, walnuts, brazil nuts, cashews, pecans, pistachios and macadamia nuts; peanuts; sesame seeds; soybeans; sulphur dioxide and sulphites. In some embodiments, the test compound is a known or potential pro-inflammatory compound, e.g., high levels of glucose; saturated fats; trans fats; Omega 6 Fatty Acids; Refined Carbohydrates; gluten/casein; aspartame; or ethanol.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, the model system is made with primary cells obtained from a healthy subject (e.g., a control), or primary cells obtained from a subject who has an inflammatory gut condition.

In some embodiments, a test compound is applied to a model system as described herein, and one or more effects of the test compound is evaluated, e.g., effects on an output of one or more biosensors of inflammation present in the system.

In some embodiments, the model system is made using cells from a subject with an inflammatory gut condition, the system can be used to determine whether the test compound exacerbates, ameliorates, or does not affect the condition in the subject.

In some embodiments, the methods include applying the test compound to the model system before, during, or after exposure to a known or suspected allergen or pro-inflammatory compound. Thus, for example, in some embodiments, the model system is made using cells from a subject with a food allergy or intolerance, and the test compound is applied to the model system in the presence of the allergen, the system can be used to determine whether the test compound exacerbates, ameliorates, or does not affect the food allergy in the subject.

Methods for evaluating each of these effects are known in the art. For example, where the output is expression of a protein or a gene, an effect can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect.

Where the output is a detectable signal such as a colorimetric change or fluorescence, known methods of microscopy and imaging can be used.

The methods can also include contacting the cells of the model with detectably labeled (e.g., fluorescently labeled) cell-type specific antibodies to allow for identification of cells in which the various sensors are activated. For example, MUC2, specifically expressed in goblet cells; LYZ, expressed in Paneth's cells; Sucrase Isomaltase expressed in mature enterocytes; CHGA, expressed in enteroendocrine cells; and GP2 and UEA-1, that label M-Cells, can be used.

A test compound that has been screened by a method described herein and determined to reduce expression or levels of a reporter triggered by an inflammatory signal can be considered a candidate compound or a "hit". A candidate compound, which can optionally be further screened in an in vivo animal or human model and determined to have a desirable effect on the gut inflammatory disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with gut inflammation as described herein, e.g., IBS, IBD, or CD. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can optionally be screened by administration to an animal model of a disorder associated with gut inflammation as described herein, e.g., IBS, IBD, or CD, as described herein. The animal can be monitored for a change in the disorder, e.g., for an improvement in a parameter of the disorder, e.g., a parameter related to clinical outcome. In some embodiments, the parameter is body weight, blood in stools, changes in stool consistency, gut inflammation, fecal calprotectin, cytokines profiling, and mortality for IBD; changes in stool consistency, serum anti-tissue transglutaminase (tTG) and anti-deamidated anti-gliadin antibodies (DGA), changes in histological parameters, including villous/crypt ratio for CD and; intestinal transit time and stool consistency in IBS, and an improvement would be maintaining body weight, absence of blood in stools, normal intestinal histology, normal fecal calprotectin levels, normal cytokine profiling for IBD, normal stool consistency, absence of tTG and/or DGA, normal villous/crypt ratio for CD and normal transit time for IBS. In some embodiments, the subject is a human, e.g., a human with IBD, CD, or IBS, and the parameter is body weight, blood in stools, change in stool consistency, gut inflammation, fecal calprotectin, cytokines profiling, and PUCAI score (specific for pediatric ulcerative colitis) for IBD; changes in stool consistency, resolution of symptoms (both intestinal and extra-intestinal) normalization of serum tTG and/or DGA, changes in histological parameters, including villous/crypt ratio for CD; and normalization of intestinal transit time and stool consistency in IBS.

The methods can also be used to identify compounds that have a pro-inflammatory effect, e.g., to identify foods or other factors that should be avoided. For example, when the primary cells are obtained from a subject, the methods can be used to identify substances that the subject from whom the primary cells were obtained should be counseled to avoid, e.g., to identify foods or proteins that the subject is allergic or intolerant to.

EXAMPLES

The invention is further described in the following examples, which do not limit the scope of the invention described in the claims.

Isolation of Duodenal Crypts and Establishment of Culture of Human Organoids

Duodenal biopsies from NC (n=5) and CD (n=6) patients were collected by upper endoscopic procedure performed for routine diagnosis or clinical follow-up. CD diagnosis was confirmed by histopathologic analysis and levels of tTG IgA blood antibodies, whereas NC patients presented normal duodenal mucosa with no evidence for CD. Patients in both groups had comparable average age (NC=56.2±13.3 years and CD=54.6±20.6 years) and gender distribution, with female donors in the majority (70%).

After collection, biopsies were immediately placed in ice-cold DMEM/F12 complete medium and processed for isolation of intestinal epithelial cells or frozen for further gene expression analysis. The isolation of intestinal epithelial cells was performed as previously described (Jung et al., Nat Med 17, 1225-1227 (2011); Senger et al., Cell Mol Gastroenterol Hepatol 5, 549-568 (2019); VanDussen et al, Gut 64, 911-920 (2015)). The duodenal organoids' culture was passaged every 7-9 days using a standard, trypsin-based cell dissociation protocol. About $2*10^6$ cells/mL singles were re-plated in matrigel supported by L-WRN/ISC medium (Senger et al., 2018) and kept at passages ranging from P5 to P22.

Duodenal Organoid-Derived Monolayers and Experimental Procedures

Organoid-derived monolayers were established by seeding $1\times10^5$ single cells from the matrigel cultures in 100 µl L-WRN/ISC medium per well on an uncoated polyester membrane transwell inserts with a 0.4 µm pore size (24 well plate, #3470, Corning, USA). The L-WRN/ISC medium was freshly supplemented with Y-27623 Rock inhibitor and changed every other day. TEER measurements and microscope direct observation were employed to monitor confluence. In order to promote cell differentiation and maturation, the confluent monolayers were apically treated with 5 µM DAPT (#565784, Calbiochem) in DMEM/F12 for 48 hours19, whereas basolateral media contained L-WRN/ISC medium only.

In some experiments, monolayers were apically pre-treated, along with DAPT, with the following: lactate, butyrate, or PSA for 48 hours, followed by media change DMEM/F12 and subsequently challenged with PTG at 1 mg/mL5 for 4 hours. Basolateral supernatant was collected for analysis. Experiments were performed at least three times in triplicates.

Organoid Growth Evaluation

To examine organoid growth over time, patient and control organoids were plated at $5\times10^4$ cells/mL and cultured for 7 days. Multiple fields per sample were acquired at 2, 4 and 7 days after plating using a bright field direct microscope (Invertoskop 40 C, Zeiss, Oberkochen, Germany). We calculated the area of the organoids ($\mu m^2$) in the captured microfield using ImageJ Software (National Institute of Healthy, USA) and then averaged the areas based on the total number of the measured organoids.

Measurement of Integrity and Paracellular Permeability of the Monolayers

TEER was evaluated during development of the monolayers and after PTG challenge as a quantitative measure of barrier integrity (Srinivasan et al, J Lab Autom 20, 107-126 (2015)). A dual planar electrode instrument (Endhom Evom, World Precision Instruments, USA) was employed according to manufacturer's directions. Data were expressed as resistance multiplied by the area ($\Omega*cm^2$).

Paracellular permeability was evaluated by measuring the diffusion of two different molecular size neutral molecules: FITC-dextran, molecular weight of 4,000 Da (#FD4 Sigma-Aldrich) and FITC-PEG of 400 Da (#PG1-FC-400, Nanocs, USA). FITC-dextran or FITC-PEG was added apically at 1 mg/ml and measured in the basolateral media after 4 hours by spectrophoto fluorimetry (Synergy 2, Biotek, USA) (485/528 nm excitation/emission wavelength), as previously reported (Fiorentino et al, Infect Immun 81, 876-883 (2013)).

Example 1

Organoid-Derived Monolayers Transduced with a Lentiviral Vector

Organoid-derived monolayers were transduced with a prototype of Lentiviral vector carrying a GFP gene under the control of the house keeping gene promoter EF1a. Organoids were dissociated with trypsin and plated in transwell as previously done (Freire et al. (2019)). Standard protocols for preparation of lentiviral particles and standard transduction protocol was adopted. Multiple lentiviral particles MOI (1:10-1:80) were tested to evaluate toxicity and efficiency of lentiviral transduction protocol. Optimized procedures using MOI: 1:10, generated about 60-90% efficiency and no cell death (see FIGS. 4A-B). Similar results were obtained across organoids derived from different donors.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An ex vivo model system, comprising: a monolayer consisting of differentiated mammalian epithelial cells, wherein the monolayer consists of enterocytes with microvilli, mucus-producing goblet cells, and Microfold (M) cells, having an apical surface and a basolateral surface, and wherein cells of the monolayer express one or more exogenous biosensors responsive to an inflammation-related signal comprising at least one promoter that binds to the inflammation-related signal and drives expression of a detectable output protein upon binding of the inflammation-related signal to the promoter wherein the differentiated mammalian epithelial cells are generated by a method comprising: obtaining primary stem cells from a mammalian subject; culturing the primary cells under conditions sufficient to allow proliferation of the cells and formation of organoids; seeding the cells of the organoid into a culture plate comprising a permeable support device; maintaining the cells underconditions to allow for sufficient proliferation to form a monolayer having an apical and basolateral surface; contacting the apical surface with DAPT and the basolateral surface with RANKL, in amounts sufficient to induce differentiation of the cells to form enterocytes with microvilli, mucus-producing goblet cells, and M cells.

2. The ex vivo model system of claim 1, wherein the primary cells are obtained from the intestine of the subject.

3. The ex vivo model system of claim 2, wherein the primary stem cells comprise intestinal crypt cells.

4. The ex vivo model system of claim 1, wherein cells of the monolayer express a plurality of biosensors, wherein each biosensor drives a different detectable output protein.

5. The ex vivo model system of claim 4, wherein the different detectable output proteins are fluorescent proteins.

6. The ex vivo model system of claim 5, wherein the different detectable output proteins comprise a plurality of different fluorescent proteins of different colors.

7. The ex vivo model system of claim 1, wherein the biosensor is responsive to an inflammation-related gene selected from the group consisting of IL-1$\beta$, TNF-$\alpha$, IFN-$\gamma$, IL-10, IL-12, IL-6, or IL-8, and the promoter comprises a promoter from the inflammation-related gene.

\* \* \* \* \*

UNITED STATES PATENT AND TRADEMARK OFFICE
CERTIFICATE OF CORRECTION

| | | |
|---|---|---|
| PATENT NO. | : 11,926,849 B2 | Page 1 of 1 |
| APPLICATION NO. | : 16/834727 | |
| DATED | : March 12, 2024 | |
| INVENTOR(S) | : Alessio Fasano et al. | |

It is certified that error appears in the above-identified patent and that said Letters Patent is hereby corrected as shown below:

On the Title Page

Column 2 (item (57) Abstract), Line 1, delete "interstinal" and insert -- intestinal --

In the Claims

In Column 14, Line 5, Claim 1, delete "underconditions" and insert -- under conditions --

Signed and Sealed this
Seventeenth Day of September, 2024

Katherine Kelly Vidal
*Director of the United States Patent and Trademark Office*